United States Patent
Zhang et al.

(10) Patent No.: US 8,965,526 B2
(45) Date of Patent: Feb. 24, 2015

(54) ACTIVE REJECTION OF MRI GRADIENT SIGNALS IN AN IMPLANTABLE MEDICAL DEVICE

(71) Applicant: Pacesetter, Inc., Sylmar (CA)

(72) Inventors: Jin Zhang, Porter Ranch, CA (US); Erno Klaassen, Los Altos, CA (US)

(73) Assignee: Pacesetter, Inc., Sylmar, CA (US)

( * ) Notice: Subject to any disclaimer, the term of this patent is extended or adjusted under 35 U.S.C. 154(b) by 94 days.

(21) Appl. No.: 13/648,958

(22) Filed: Oct. 10, 2012

(65) Prior Publication Data
US 2014/0100637 A1   Apr. 10, 2014

(51) Int. Cl.
*A61N 1/08* (2006.01)
*A61N 1/36* (2006.01)
*A61N 1/37* (2006.01)

(52) U.S. Cl.
CPC ......... *A61N 1/3718* (2013.01); *A61N 2001/086* (2013.01); *A61N 1/08* (2013.01)
USPC .................................. 607/62; 607/63; 607/2

(58) Field of Classification Search
USPC ............................................. 607/4, 6, 62–63
See application file for complete search history.

(56) References Cited

U.S. PATENT DOCUMENTS

| | | | |
|---|---|---|---|
| 4,712,555 A | 12/1987 | Thornander et al. | |
| 4,940,052 A | 7/1990 | Mann et al. | |
| 4,944,298 A | 7/1990 | Sholder | |
| 5,466,254 A | 11/1995 | Helland | |
| 5,476,483 A | 12/1995 | Bornzin et al. | |
| 7,123,013 B2 | 10/2006 | Gray | |
| 7,742,825 B2 | 6/2010 | Gray et al. | |
| 2004/0263172 A1* | 12/2004 | Gray et al. | 324/322 |
| 2004/0263173 A1 | 12/2004 | Gray | |
| 2004/0263174 A1 | 12/2004 | Gray et al. | |
| 2008/0058913 A1 | 3/2008 | Gray et al. | |
| 2008/0079429 A1 | 4/2008 | Gray | |
| 2010/0152805 A1 | 6/2010 | Zeijlemaker | |

FOREIGN PATENT DOCUMENTS

| | | |
|---|---|---|
| WO | 9221286 | 12/1992 |
| WO | 2005003790 A2 | 1/2005 |
| WO | 2005003790 A3 | 12/2005 |

* cited by examiner

*Primary Examiner* — Carl H Layno
*Assistant Examiner* — Jon Eric C Morales

(57) ABSTRACT

Active rejection techniques are used to cancel MRI gradient signals in an implantable medical device. An active component placed in an input channel of the implantable medical device actively rejects MRI gradient signals received on the input channel. A sensing circuit that senses an external MRI gradient signal generates a control signal that controls the active component. For example, the control signal may be the inverse of the external MRI gradient signal. An active component that receives an input signal including a desired signal component (e.g., a cardiac signal) and an undesired MRI gradient signal component may thus use this control signal to reject the undesired MRI gradient signal component.

17 Claims, 9 Drawing Sheets

ACTIVE REJECTION OF MRI GRADIENT SIGNALS IN AN IMPLANTABLE MEDICAL DEVICE

TECHNICAL FIELD

This application relates generally to implantable medical devices and more specifically, but not exclusively, to active rejection of MRI gradient signals.

BACKGROUND

Some types of implantable medical devices are used in conjunction with one or more implantable leads. For example, a cardiac rhythm management device (e.g., a pacemaker, a defibrillator, or a cardioverter defibrillator) implanted at a subcutaneous site may connect to one or more leads that terminate at or near the heart of a patient. Through the use of such a lead, the device is able to effectively monitor cardiac function and provide stimulation therapy for a patient who suffers from cardiac arrhythmia.

If a patient with a lead-based implantable medical device is subjected to magnetic resonance imaging ("MRI") scanning, the device could malfunction in some cases. For example, time-varying magnetic fields generated during an MRI scan may induce current in an implanted lead. A relatively large current and/or voltage may be generated at the implantable medical device as a result of this induced lead current. In some cases, this current and/or voltage may affect the internal circuitry of the implantable medical device and cause the device to malfunction.

In an attempt to address such MRI issues, implantable medical devices may incorporate an MRI radiofrequency (RF) filter that is tuned to filter out strong MRI-induced RF signals (e.g., in the range of 64 MHz and 128 MHz). Such a filter may be incorporated into an implantable lead and/or in an implantable device.

In practice, however, these MRI RF filters may not adequately filter MRI gradient signals (e.g., depending on the manufacturer and MRI scanner model, MRI gradient signals may have a major bandwidth from hundreds of hertz up to several hundred kilohertz). Of note here, the MRI gradient signal frequency range is relatively close to the frequency range of sensed cardiac signals (e.g., 100 Hz or less). Moreover, the amplitude of the MRI gradient signal may be much larger than the magnitude of a sensed cardiac signal. Thus, the MRI gradient signal may swamp the receive amplifiers of the implantable medical device in some cases, thereby preventing the implantable medical device from being able to accurately detect other incoming signals (e.g., cardiac signals). Hence, it is relatively difficult to design a filter that efficiently rejects the MRI gradient signal and allows the desired cardiac signals to pass in all cases. Accordingly, there is a need for a technique that effectively rejects MRI gradient signals in implantable medical devices.

SUMMARY

A summary of several sample aspects of the disclosure and embodiments of an apparatus constructed or a method practiced according to the teaching herein follows. It should be appreciated that this summary is provided for the convenience of the reader and does not wholly define the breadth of the disclosure. For convenience, one or more aspects or embodiments of the disclosure may be referred to herein simply as "some aspects" or "some embodiments."

The disclosure relates in some aspects to active rejection of MRI gradient signals in an implantable medical device. For example, an active component may be placed in each input channel of an implantable medical device to actively reject MRI gradient signals received on those input channels. A sensing circuit that senses an external MRI gradient signal generates a corresponding control signal that controls each active component.

In some embodiments, the control signal is the inverse of the external MRI gradient signal. For example, the sensing circuit may be configured to filter out substantially all received signals other than an MRI gradient signal and generate a control signal that is 180 degrees out-of-phase with the MRI gradient signal. In this case, an active component that receives an input signal including a desired signal component (e.g., a cardiac signal) and an undesired MRI gradient signal component may essentially add the control signal to the received signal to thereby reject the undesired MRI gradient signal component.

Accordingly, in some embodiments, an apparatus for rejecting MRI gradient signals in an implantable medical device comprises a detector circuit and an MRI gradient active rejection circuit. The detector circuit is configured to detect an MRI gradient signal and generate a control signal based on the detected MRI gradient signal. The MRI gradient active rejection circuit is configured to reject an MRI gradient signal component of a signal received via an implantable lead to provide an output signal, wherein the rejection of the MRI gradient signal component is based on the control signal.

In some embodiments, the active component comprises a transistor circuit that is biased within a linear region for MRI gradient rejection, whereby the control signal causes the transistor to reject an undesired MRI gradient signal component of a received signal. Advantageously, such a transistor circuit may also serve as a high frequency protection switch in some embodiments. That is, whenever a high voltage input signal is detected or anticipated, the transistor circuit may be biased (e.g., biased off) to reject all incoming signals.

BRIEF DESCRIPTION OF THE DRAWINGS

These and other aspects of the disclosure will be more fully understood when considered with respect to the following detailed description, the appended claims, and the accompanying drawings, wherein:

Figure 1:
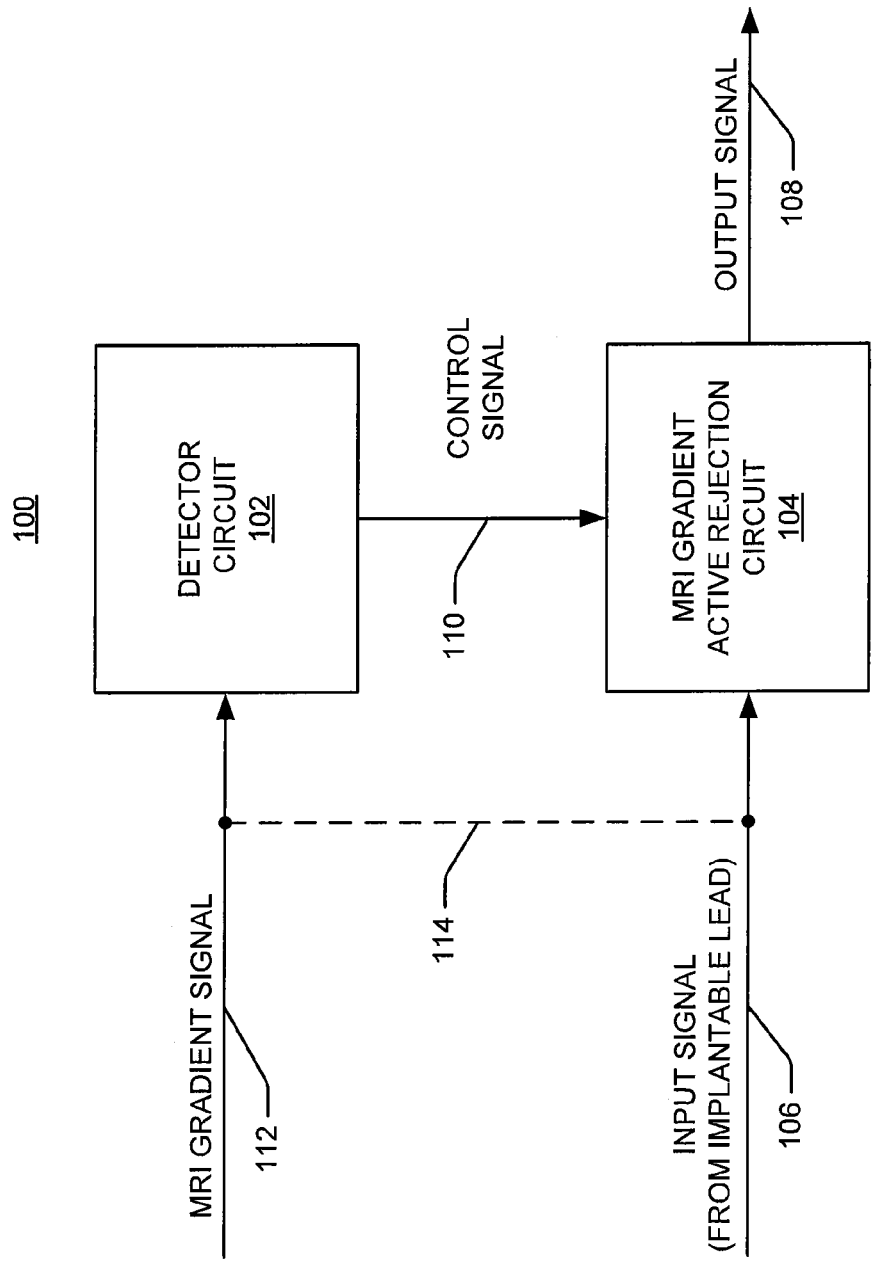
FIG. 1 is a simplified block diagram of an embodiment of an apparatus for rejecting MRI gradient signals.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

FIG. 1 illustrates an embodiment of an apparatus 100 comprising a detector circuit 102 and an MRI gradient active rejection circuit 104. These circuits cooperate to reject an MRI gradient signal component from a received signal to provide an output signal. In a typical case, this signal is received via an implantable lead (not shown in FIG. 1) that is connected to an implantable medical device within which the apparatus is deployed.

In the example of FIG. 1, the MRI gradient active rejection circuit 104 receives the input signal via a conductor 106. For example, the conductor 106 may be coupled (directly or through other components) to an implantable lead. The input signal will include a signal component of interest (e.g., a cardiac signal in an implementation where the implantable lead is a cardiac lead) and, whenever the implantable medical device is subjected to MRI scanning, an unwanted MRI gradient signal component.

The operation of the MRI gradient active rejection circuit 104 depends on whether the implantable medical device is currently subjected to MRI scanning. If the implantable medical device is not subjected to MRI scanning, the MRI gradient active rejection circuit 104 may simply pass the received signal unchanged (or pass an amplified version of the received signal) to provide the output signal. However, if the implantable medical device is subjected to MRI scanning, the MRI gradient active rejection circuit 104 rejects the MRI gradient signal component from the input signal to produce an output signal on a conductor 108. As discussed in more detail below, the operation of the MRI gradient active rejection circuit 104 is based on a control signal received from the detector circuit 102 via a conductor 110.

The detector circuit 102 generates the control signal based on detection of an MRI gradient signal received via a conductor 112. The conductor 112 is coupled to an input of the detector circuit and configured to acquire an MRI gradient signal if the implantable medical device is subjected to an MRI field. For example, in some embodiments, the conductor 112 may be located at a location and formed with a sufficient size and shape that facilitates inducement of an MRI gradient signal on the conductor 112 whenever the implantable medical device is subjected to MRI scanning. In other embodiments, the conductor 112 may be coupled to the conductor 102 (e.g., via the optional conductor 114) or some other conductor that is coupled to an implantable lead.

The detector circuit 102 will generally not detect the signal of interest, however. For example, in embodiments where the conductor 112 is isolated from cardiac tip and ring conductors of an implantable lead that that is used to acquire cardiac signals, the signal received by the detector circuit may not include a cardiac signal component. As another example, in embodiments where the conductor 112 is coupled to an implantable lead, the detector circuit 102 may include a filter circuit to filter out the signal of interest (e.g., by filtering out signals of 200 Hz or less). In some embodiments, the filter circuit may be configured to filter out signals that are below and/or above the MRI gradient signal frequency band. As one non-limiting example, in a scenario where the MRI signals frequencies of interest are above 100 kHz, the filter circuit may filter out signals below 100 KHz. It should be appreciated that the frequencies stated above are for purposes of illustration. In practice, a system constructed according to the teachings herein may filter out a different range of frequencies in other scenarios.

The value of the control signal at a given point in time depends on whether the detector circuit 102 has detected an MRI gradient signal. If an MRI gradient signal is not detected, the detector circuit 102 sets the control signal to a value that causes the MRI gradient active rejection circuit 104 to not apply MRI gradient rejection (e.g., the input signal is simply passed to the output).

If an MRI gradient signal is detected, the detector circuit 102 sets the control signal to a value that causes the MRI gradient active rejection circuit 104 to perform MRI gradient rejection. Advantageously, the MRI gradient signal detected by the detector circuit 102 will generally be substantially similar to the MRI gradient component of the signal induced on the implantable lead and, hence, received via the conductor 106. Consequently, the detector circuit 102 may generate the control signal in a manner that enables the MRI gradient active rejection circuit 104 to reject (e.g., all or substantially all of) the MRI gradient component.

In some embodiments, the control signal comprises the inverse of the MRI gradient signal. That is, the control signal is generated so that it is substantially 180 degrees out-of-phase with the MRI gradient signal and, in some cases, equal in amplitude to the MRI gradient signal. In such a case, the MRI gradient active rejection circuit 104 may effectively reject the MRI signal component of the input signal by essentially adding the control signal to the received signal.

The apparatus 100 is implemented in conjunction with an implantable medical device (not shown in FIG. 1) to reject MRI gradient signals that could otherwise adversely affect the operation of internal components of the implantable medical device. As discussed herein, the apparatus 100 typically is implemented entirely within the housing of an implantable medical device. In some embodiments, however, the apparatus may be implemented partially within the housing and partially outside of the housing (e.g., partially within a header and/or a lead). In still other embodiments, the apparatus may be implemented entirely outside of the housing (e.g., within a header and/or or a lead).

The detector circuit 102 may be implemented in different ways in different embodiments. In some embodiments, the detector circuit 102 comprises an amplifier circuit. In some embodiments, the detector circuit 102 comprises a filter circuit having a bandwidth of less than 5 MHz. In some embodiments, the detector circuit 102 comprises a filter circuit having a bandwidth of less than 1 MHz. As one non-limiting example, in a scenario where the MRI signal frequencies of interest are centered around 200 kHz, the detector circuit 102 provides bandpass filtering having a center frequency of approximately 200 kHz. In this way, the detector circuit 102 may be configured to only detect the MRI gradient signal band. It should be appreciated that in different embodiments the detector circuit 102 may have different filter properties than those listed above. That is, the frequencies stated above are for purposes of illustration (e.g., the 200 KHz example is a demonstrative example). In practice, a system constructed according to the teachings herein may filter out a different range of frequencies in other scenarios.

The MRI gradient active rejection circuit 104 may be implemented in different ways in different embodiments. In some embodiments, the circuit 104 comprises an amplifier circuit. As discussed in more detail below, in some embodiments, the circuit 104 comprises a transistor circuit that is biased to operate within an active (i.e., linear) region if the implantable medical device is subjected to an MRI field. Such a transistor circuit may comprise, for example, a metal oxide semiconductor (MOS) transistor, an insulated gate bipolar transistor (IGBT), a bipolar junction transistor (BJT), an internal CMOS circuit in an integrated circuit, or some other suitable active component(s).

Figure 2:
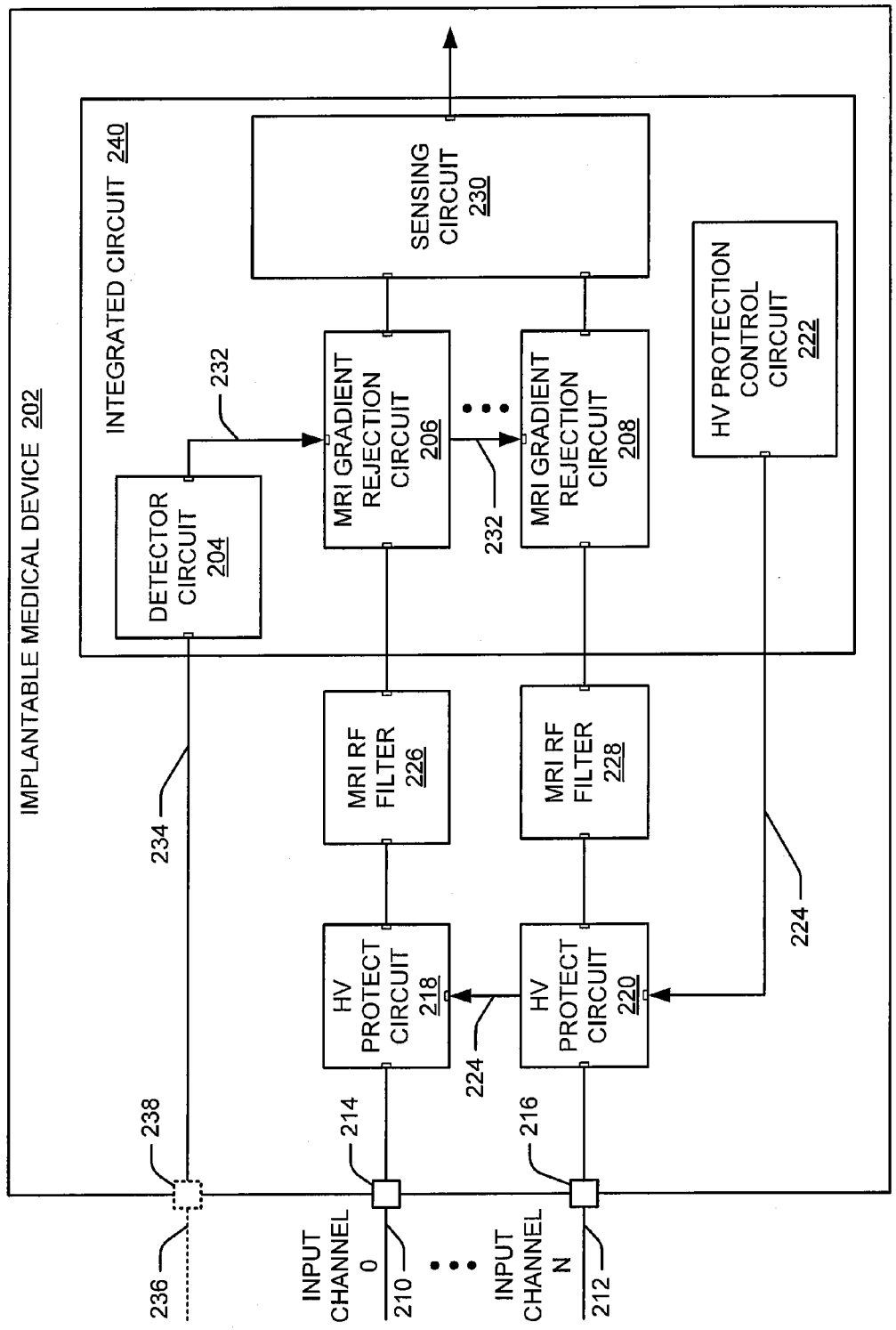
FIG. 2 is a simplified block diagram of an embodiment of an implantable medical device illustrating one configuration for MRI gradient signal rejection circuitry.
Figure 3:
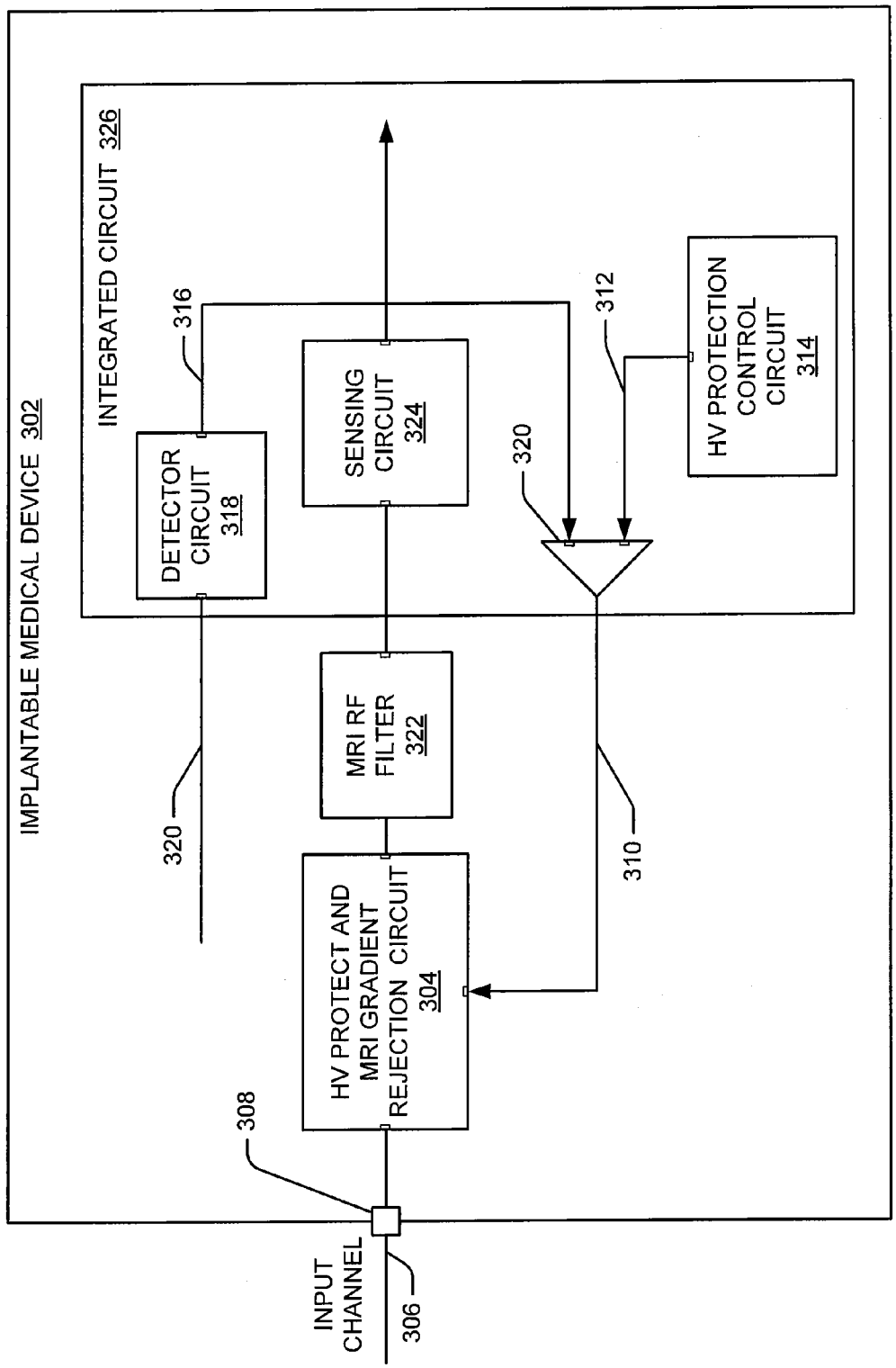
FIG. 3 is a simplified block diagram of an embodiment of an implantable medical device illustrating another configuration for MRI gradient signal rejection circuitry.

FIGS. 2 and 3 illustrate two examples of how the detector circuit 102 and the MRI gradient active rejection circuit 104 may be implemented in implantable medical devices. In particular, FIG. 2 illustrates an embodiment where an MRI gradient rejection circuit is placed after an MRI filter in each input channel. FIG. 3, on the other hand, illustrates an embodiment where an MRI gradient rejection circuit is integrated with a high voltage (HV) protection circuit in an input channel.

Referring initially to FIG. 2, an implantable medical device 202 includes a detector circuit 204 (e.g., corresponding to the detector circuit 102) and several MRI gradient rejection circuits (e.g., each of which corresponds to the MRI gradient active rejection circuit 104). One MRI gradient rejection circuit is provided for each input channel. In this example, the input channels are designated 0-N and the corresponding MRI gradient rejection circuits are represented by MRI gradient rejection circuits 206-208 and the associated ellipsis.

In the simplified illustration of FIG. 2, each input channel receives signals via an external conductor (represented by external conductors 210-212 and the associated ellipsis) that may, for example, correspond to a conductor of an implantable lead. Each external conductor connects to a respective connector (represented by connectors 214-216) of the implantable medical device 202.

The external conductors 210-212 may be in the same lead or may be in different leads depending on the particular implementation being used. Consequently, the connectors 214-216 may be part of a common connector housing (e.g., a bipolar IS-1 connector) or separate connector housings.

Each input channel includes a high voltage protection circuit (represented by HV protect circuits 218-220) that is coupled to a respective one of the connectors 214-216. The high voltage protection circuits block incoming signals whenever high voltage signals are detected or anticipated at the implantable medical device 202.

A HV protection control circuit 222 generates a control signal 224 that controls the high voltage protection circuits 218-220. Under normal operating conditions, the HV protection control circuit 222 sets the control signal 224 to a value that causes the high voltage protection circuits 218-220 to pass all incoming signals. Upon detection or anticipation of a high input voltage, however, the HV protection control circuit 222 sets the control signal 224 to a value that causes the high voltage protection circuits 218-220 to reject incoming signals (e.g., all or substantially all of the incoming signals are rejected or attenuated). The HV protection control circuit 222 may invoke high voltage protection upon detecting a voltage on an input channel that exceeds a predefined magnitude (e.g., that could potentially damage the components of the implantable medical device 202). As another example, the HV protection control circuit 222 may invoke high voltage protection upon receiving an indication that the implantable medical device 202 will be generating a high voltage shocking pulse (e.g., for cardiac shock therapy).

Figure 5:
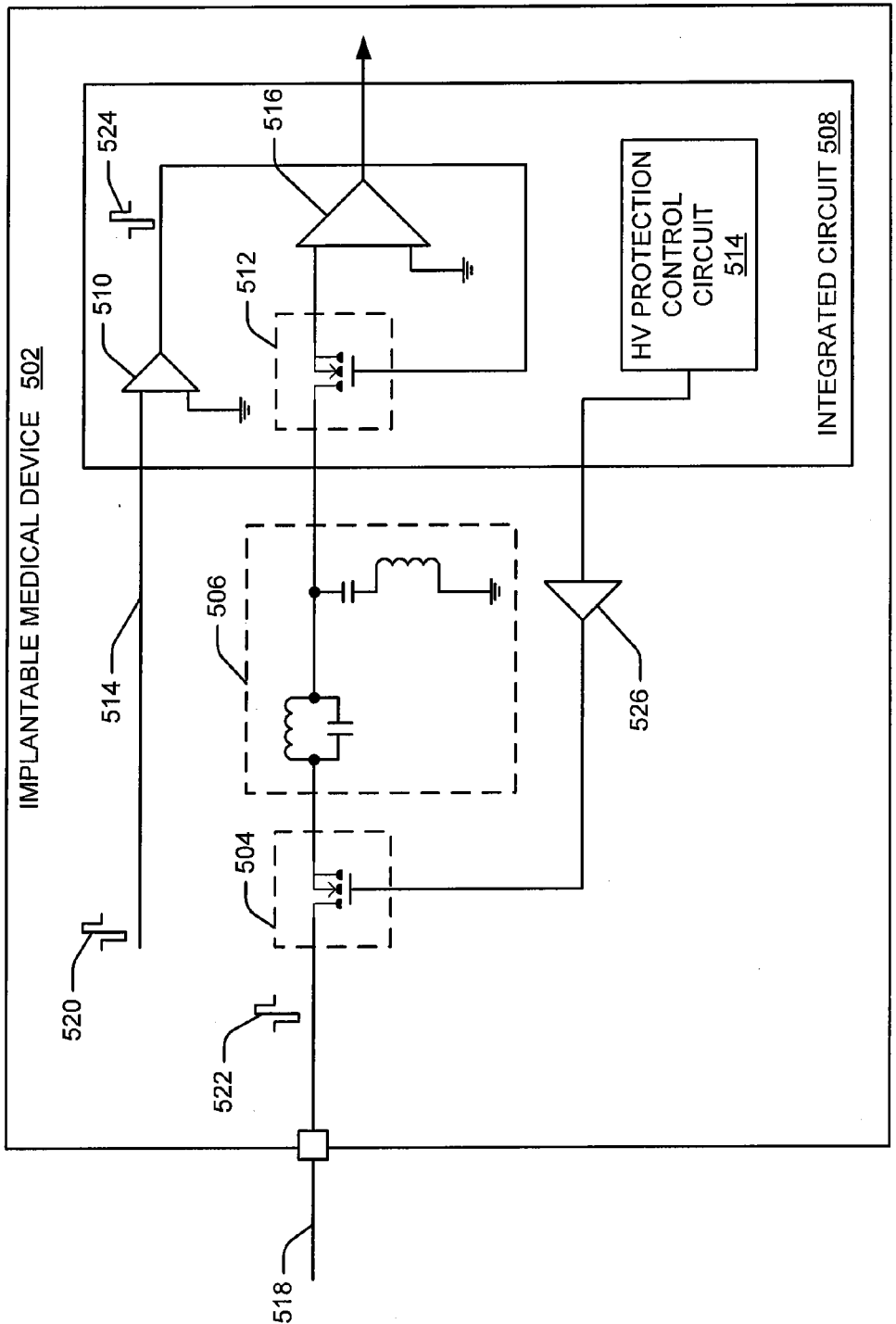
FIG. 5 is a simplified diagram of an embodiment of an implantable medical device illustrating one example of MRI gradient signal rejection circuitry.
Figure 6:
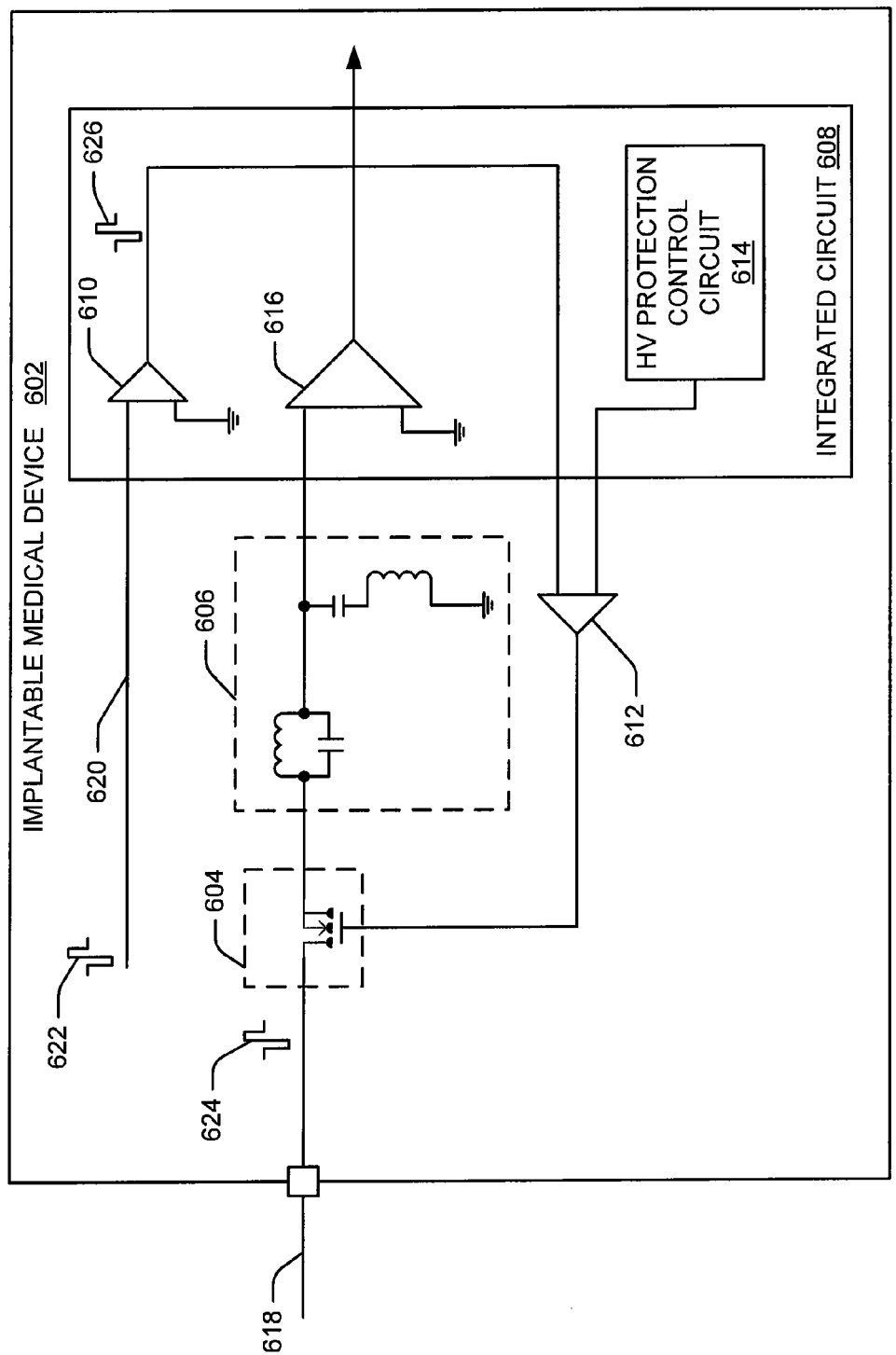
FIG. 6 is a simplified diagram of an embodiment of an implantable medical device illustrating another example of MRI gradient signal rejection circuitry.

Each input channel also includes an MRI RF filter circuit (represented by MRI RF filters 226-228) that is coupled to a respective one of the HV protection circuits 218-220. Thus, an input terminal of each MRI RF filter circuit is coupled to a respective one of the external conductors 210-212 to receive the signals for a corresponding input channel. The MRI RF filter circuits are configured to attenuate any MRI RF signals (e.g., centered around 64 MHz and/or 128 MHz) that may be present in the input channel signals. An example of an MRI RF filter circuit is shown in FIGS. 5 and 6.

The MRI gradient rejection circuits 206-208 are located between the MRI RF filter circuits and the sensing circuit 230. An input terminal of each of the MRI gradient rejection circuits is coupled to an output terminal of a respective one of the MRI RF filter circuits. An output terminal of each of the MRI gradient rejection circuits is coupled to a respective input terminal of the sensing circuit 230. These terminals are represented by the small boxes adjacent the conductors between the circuits in FIG. 2.

In the presence of MRI scanning, each of the MRI gradient rejection circuits 206-208 reject the MRI gradient signal component of a signal received via a respective input channel. For example, the MRI gradient rejection circuit 206 receives a filtered signal for input channel 0 from the MRI RF filter 226. The MRI gradient rejection circuit 206 rejects an MRI gradient signal component of this signal to provide a signal to the sensing circuit 230. The signal provided to the sensing circuit 230 will thus comprise the desired signal component (e.g., cardiac signal sensed via the conductor 210) and little or no MRI gradient signal component. Consequently, the sensing circuit 230 will be able to accurately detect a desired signal even when the implantable medical device 202 is subjected to MRI scanning.

Moreover, in practice, the amplifier circuitry of the sensing circuit 230 will filter out frequencies above the desired signal component frequencies (e.g., filter out frequencies above 200 Hz for the case of sensed cardiac signals). Consequently, the MRI gradient rejection need not reject the MRI gradient signal component in its entirely to achieve satisfactory operation. At a minimum, the MRI gradient signal component should be rejected to a sufficient degree so that the amplifiers of the sensing circuit 230 are not saturated by the MRI gradient signal component.

The detector circuit 204 generates a control signal 232 that controls the MRI gradient rejection provided by each MRI gradient rejection circuit 206-208. For example, if an MRI gradient signal is detected by the detector circuit 204, the control signal 232 may comprise an inverse of that MRI gradient signal as discussed above. In the event such an MRI gradient signal is not detected, the value of the control signal 232 (e.g., a steady state value) may cause each MRI gradient rejection circuit to simply pass a received signal (e.g., the received signal is passed unchanged or is only amplified).

The detector circuit 204 detects the MRI gradient signal via a conductor 234. In some embodiments, the conductor 234 resides entirely within the implantable medical device 202 and acquires MRI gradient signals either by itself (e.g., due to its location, length and shape) or by connection to another conductor (e.g., at an input of a HV protect circuit or an output of an MRI RF filter circuit) onto which MRI gradient signals may be coupled. In other embodiments, as represented by the external conductor 236 and the connector 238 shown in dashed lines in FIG. 2, the conductor 234 is coupled to an external conductor (e.g., in an implantable lead) that will acquire MRI gradient signals. As mentioned above, in some embodiments, the detector circuit 204 includes filter circuitry for filtering out the desired cardiac signal of interest from the signal received by the detector circuit 204.

In some embodiments, one or more of the circuits 204, 206-208, 222, and 230 are implemented in a common device. For example, these circuits may be implemented in an integrated circuit 240 that includes analog circuitry and, optionally, digital circuitry.

Referring now to FIG. 3, this embodiment illustrates that MRI gradient rejection circuitry and HV protection circuitry of an implantable medical device 302 may be advantageously implemented using common circuitry. To reduce the complexity of FIG. 3, only a single input channel is shown. It should be appreciated, however, that the configuration shown in FIG. 3 typically will be employed in embodiments that have multiple input channels.

An input terminal of an HV protects and MRI gradient rejection circuit 304 is coupled to an external conductor 306 for an input channel via a connector 308. The external conductor 306 and the connector 308 may be similar to the external conductors 210-212 and the connectors 214-216 discussed above in conjunction with FIG. 2.

The circuit 304 is controlled by at least one control signal 310 that is based on a control signal 312 generated by a HV protection control circuit 314 and a control signal 316 generated by a detector circuit 318. In the example of FIG. 3, a control signal circuit 320 provides the at least one control signal 310 based on the control signals 312 and 316. For example, in different embodiments, the control signal circuit 320 may: selectively pass one of the control signals 312 and 316; generate a combined control signal based on the control signals 312 and 316; or simply pass the control signals 312 and 316 to the circuit 304.

In a typical embodiment, the control signal 312 from the HV protection control circuit 314 controls whether the circuit 304 is to block all incoming signals or is to be controlled by the control signal 316. For example, the HV protection control circuit 314 may generate the control signal 312 in a similar manner as discussed above in conjunction with FIG. 2. Thus, upon detection or anticipation of a high input voltage, the HV protection control circuit 314 causes the circuit 304 to reject incoming signals. That is, based on the control signal 312, the control signal circuit 320 sets the at least one control signal 310 to a value that causes the circuit 304 to reject all or substantially all incoming signals. At all other times, the circuit 304 is controlled by the control signal 316.

In a similar manner as discussed above for the detector circuit 204, the detector circuit 318 generates the control signal 316 based on detection of an MRI gradient signal. Thus, if an MRI gradient signal is detected, the control signal 316 may comprise an inverse of the MRI gradient signal detected by the detector circuit 318. Otherwise, the control signal 316 may be set to a value that causes the circuit 304 to simply pass any received signals.

The detector circuit 318 detects the MRI gradient signal via a conductor 320 in a similar manner as discussed above for the conductor 234. Thus, in some embodiments, the conductor 320 may be coupled to an external conductor (e.g., of an implantable lead).

An output terminal of the circuit 304 is coupled to an input terminal of the MRI RF filter circuit 322. The MRI RF filter circuit 322 is configured to attenuate MRI RF signals (e.g., centered around 64 MHz or 128 MHz) as discussed herein.

An output terminal of the MRI RF filter circuit 322 is coupled to an input terminal of a sensing circuit 324. A signal provided to the sensing circuit 324 will thus comprise the desired signal component (e.g., cardiac signal sensed via the conductor 306) and little or no MRI gradient signal component.

In some embodiments, one or more of the circuits 314, 318, 320, and 324 are implemented in a common device. For example, these circuits may be implemented in an integrated circuit 326 that includes analog circuitry and, optionally, digital circuitry.

Figure 4:
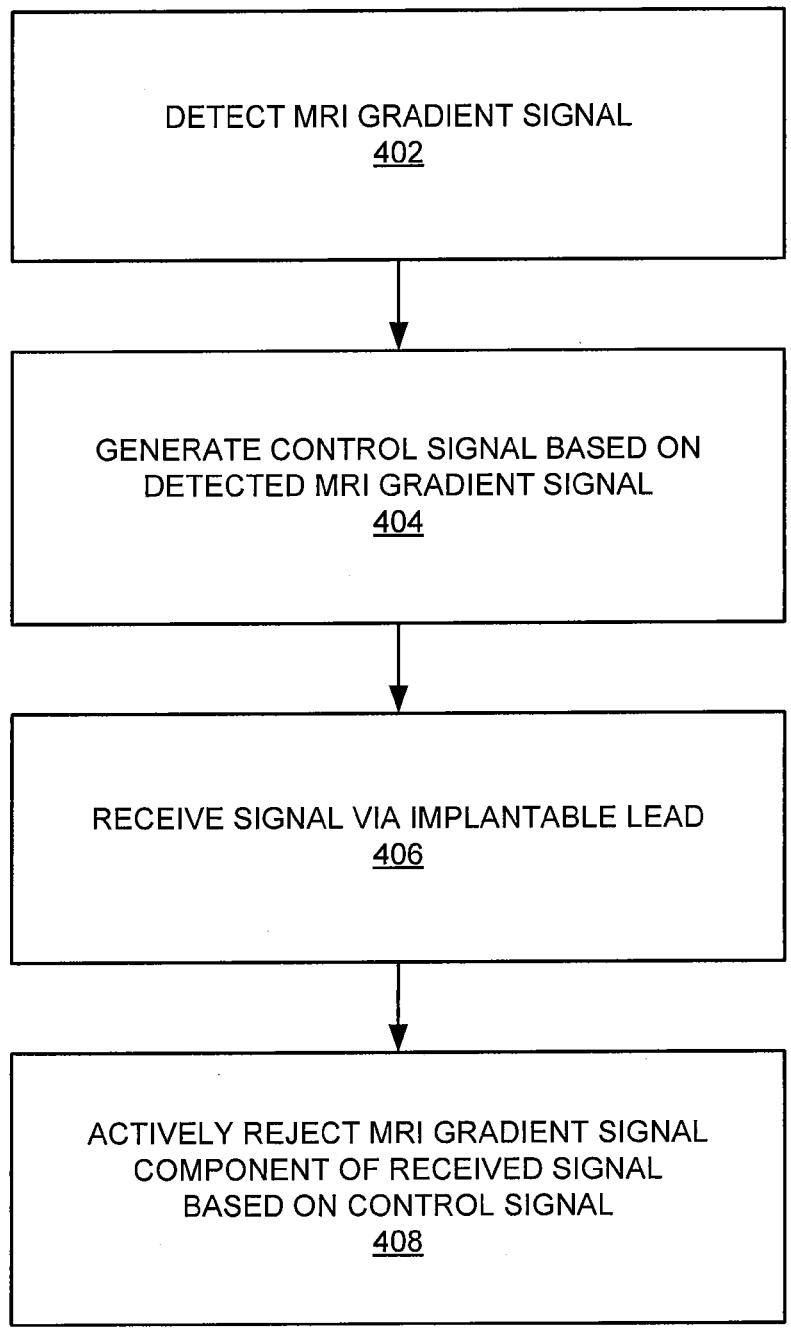
FIG. 4 is a simplified flowchart of an embodiment of operations that may be performed to reject MRI gradient signals.

With the above in mind, FIG. 4 summarizes several sample operations that may be performed to actively reject MRI gradient signals in accordance with the teachings herein. For convenience, the operations of FIG. 4 (or any other operations discussed or taught herein) may be described as being performed by specific components (e.g., the components of FIG. 1, 2, or 3). It should be appreciated, however, that these operations may be performed by other types of components and may be performed using a different number of components. It also should be appreciated that one or more of the operations described herein may not be employed in a given implementation.

Blocks 402 and 404 correspond to operations that may be performed, for example, by a detector circuit. As represented by block 402, at some point in time, an MRI gradient signal is detected. As represented by block 404, a control signal is generated based on the detected MRI gradient signal.

Blocks 406 and 408 correspond to operations that may be performed, for example, by an MRI gradient rejection circuit. As represented by block 406, concurrent with the detection of the MRI gradient signal, a signal is received via an implantable lead. As represented by block 408, an MRI gradient signal component of the received signal is actively rejected based on the control signal.

In some embodiments, the operations of FIG. 4 may be advantageously performed by analog circuitry. Accordingly, a high degree of MRI gradient rejection may be achieved with relatively low cost and relatively low power consumption. FIGS. 5 and 6 illustrate examples of how the configurations of FIGS. 2 and 3 may be implemented using specific analog circuits.

Referring initially to FIG. 5, an implantable medical device 502 includes a HV protection switch 504, an MRI RF filter 506, an integrated circuit 508, and a driver device 526. The integrated circuit 508 includes a detector circuit 510, an MRI gradient rejection circuit 512, a HV protection control circuit 514, and a sensing circuit 516.

The HV protection switch 504 comprises a transistor that is controlled by a control signal generated by the HV protection control circuit 514. When a high voltage input signal is detected or anticipated, the HV protection control circuit 514 generates a control signal that causes the driver device 526 to bias the transistor OFF (e.g., the transistor is biased to a cutoff region). In this way, any input signals received from an implantable lead 518 are not allowed to propagate to other components of the implantable medical device 502. When a high voltage input signal is not detected or anticipated, the HV protection control circuit 514 generates a control signal that causes the driver device 526 to bias the transistor ON (e.g., the transistor is biased to a saturation region). In this case, any input signals received from the implantable lead 518 are allowed to propagate to the MRI RF filter 506.

The MRI RF filter 506 comprises a pair of resonant LC circuits. The LC circuits are tuned to attenuate frequencies in a designated range. For example, the MRI RF filter 506 may attenuate frequencies in the range of 64 MHz and/or 128 MHz. Other more complex MRI RF filter topologies (e.g., including additional resonant LC circuits) may be used in other embodiments to provide more effective MRI RF filtering.

The output of the MRI RF filter 506 is coupled to the MRI gradient rejection circuit 512. In this example, the MRI gradient rejection circuit 512 comprises a transistor that is controlled by a control signal generated by the detector circuit 510. If the detector circuit 510 does not detect an MRI gradient signal via the conductor 514, the control signal biases the transistor ON such that any input signals that pass through the MRI RF filter 506 are allowed to propagate to the sensing circuit 516.

If the detector circuit 510 detects an MRI gradient signal, the control signal biases the transistor to operate within an active region (e.g., linear region) such that the MRI gradient rejection circuit 512 will reject an MRI gradient component of any input signals that pass through the MRI RF filter 506. In this way, the desired input signal (e.g., a cardiac signal with little or no MRI gradient signal component) is propagated to the sensing circuit 516.

As discussed above, the control signal generated by the detector circuit 510 may comprise an inverse of the detected MRI gradient signal. As indicated by simplified signal waveforms in FIG. 5, during MRI scanning, an MRI gradient signal 520 may be detected by the detector circuit 510. At the same time, an input signal 522 dominated by an MRI gradient component is received via the implantable lead 518. The detector circuit 510 generates a control signal 524 that is the inverse of the detected MRI gradient signal 520. Since the transistor of the MRI gradient rejection circuit 512 is operating in an active region, the output of the MRI gradient rejection circuit 512 will be based on the amplitude of this control signal. Thus, the MRI gradient rejection circuit 512 will effectively reject the dominant MRI gradient component of the input signal 522 due to the inverse property of the control signal 524. In essence, the MRI gradient rejection circuit 512 effectively adds the control signal 524 to the input signal 522 to reject the MRI gradient component of the input signal 522. Consequently, the desired input signal component is provided to the sensing circuit 516.

Referring now to FIG. 6, an implantable medical device 602 includes a HV protection and MRI gradient rejection circuit 604, an MRI RF filter 606, an integrated circuit 608, and a driver device 612. The integrated circuit 608 includes a detector circuit 610, a HV protection control circuit 614, and a sensing circuit 616.

The HV protection and MRI gradient rejection circuit 604 comprises a transistor that is controlled by control signals generated by the HV protection control circuit 614 and the detector circuit 610. The driver device 612 generates a bias signal based on these control signals to bias the transistor to the desired state depending on whether a HV input signal has been sensed or anticipated and depending on whether an MRI gradient signal has been detected.

When a high voltage input signal is detected or anticipated, the HV protection control circuit 614 generates a control signal that causes the driver device 612 to bias the transistor OFF (e.g., the transistor is biased to a cutoff region). Thus, input signals received from an implantable lead 618 are not allowed to propagate to other components of the implantable medical device 602 when this control signal is set to a value for rejecting high voltage signals. When a high voltage input signal is not detected or anticipated, the HV protection control circuit 614 generates a control signal that causes the driver device 612 to enable the control signal from the detector circuit 610 to control the bias of the transistor.

If the detector circuit 610 does not detect an MRI gradient signal via the conductor 620 and if the control signal from the HV protection control circuit 614 is not set to a value for rejecting high voltage signals, the control signal from the detector circuit 610 causes the driver device 612 to bias the transistor ON. In this case, any signals at the input of the transistor are allowed to propagate to the MRI RF filter 606.

If the detector circuit 610 detects an MRI gradient signal and if the control signal from the HV protection control circuit 614 is not set to a value for rejecting high voltage signals, the control signal from the detector circuit 610 causes the driver device 612 to bias the transistor to operate within an active region (i.e., linear region) such that the circuit 604 will reject an MRI gradient component of any input signals. In this way, the desired input signal (e.g., a cardiac signal with little or no MRI gradient signal component) is propagated to the MRI RF filter 606.

Again, the control signal generated by the detector circuit 610 may comprise an inverse of the detected MRI gradient signal. Thus, during MRI scanning, an MRI gradient signal 622 may be detected by the detector circuit 610 and an input signal 624 dominated by an MRI gradient component may be received via the implantable lead 618. The detector circuit 610 generates a control signal 626 that is the inverse of the detected MRI gradient signal 622. Since the transistor of the circuit 604 is operating in an active region, the output of the circuit 604 will be based on the amplitude of this control signal. Thus, the circuit 604 will effectively reject the dominant MRI gradient component of the input signal 624 due to the inverse property of the control signal 626.

The MRI RF filter 606 comprises a pair of resonant LC circuits. As discussed above, the LC circuits are tuned to attenuate frequencies in a designated range (e.g., around 64 MHz and/or 128 MHz). Again, other more complex MRI RF filter topologies may be used in other embodiments.

The output of the MRI RF filter 606 is coupled to the sensing circuit 616. The signal provided to the sensing circuit 616 will thus comprise the desired signal component (e.g., cardiac signal sensed via the implantable lead 618) and little or no MRI gradient signal component.

Figure 7:
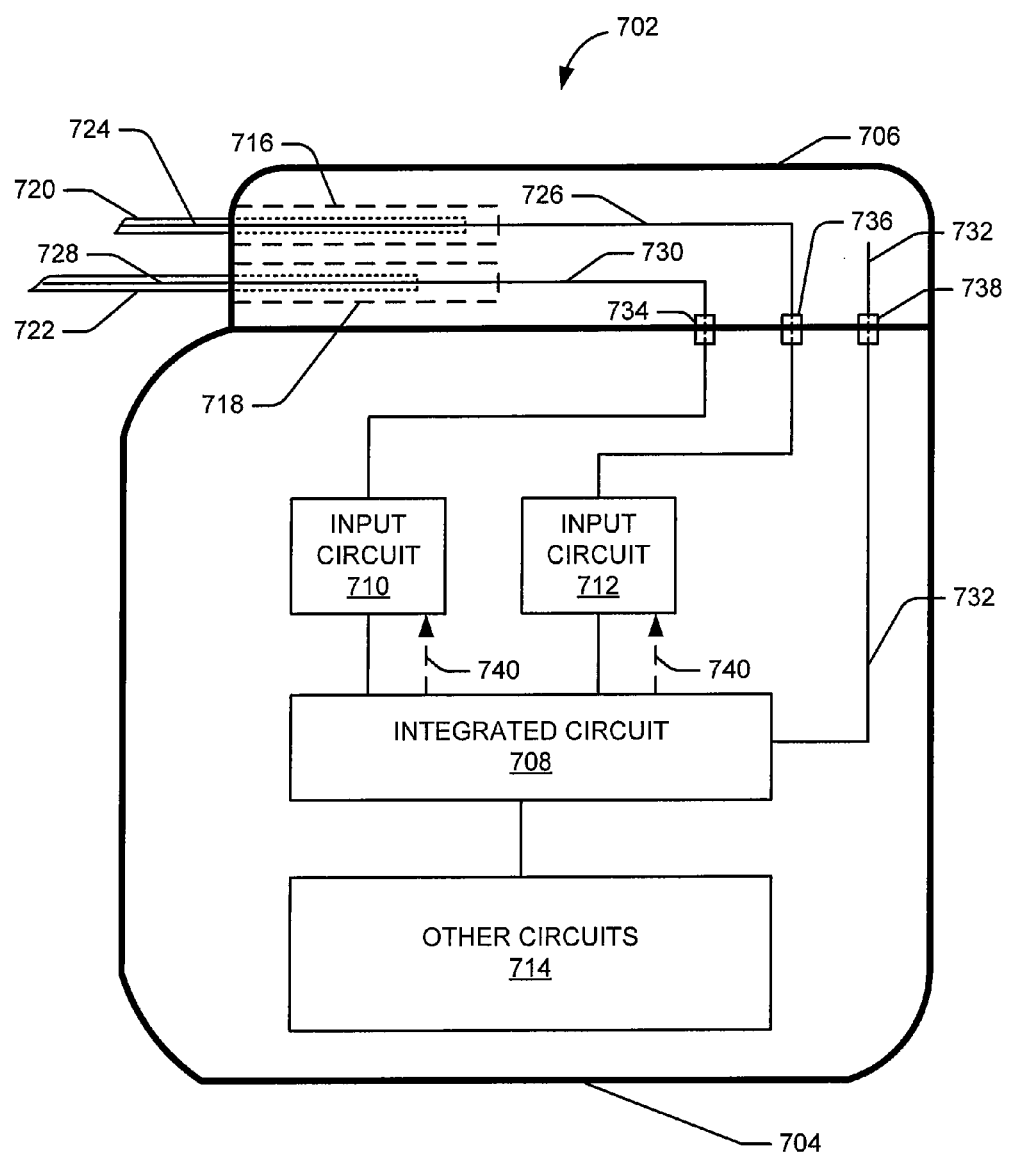
FIG. 7 is a simplified diagram of an embodiment of an implantable medical device illustrating an example of header and housing components.

FIG. 7 is a simplified example of an implantable medical device 702 that illustrates in more detail how the circuitry described herein may be coupled to one or more implantable leads. The implantable medical device 702 comprises a biocompatible and hermetically sealed housing 704 and a header 706.

The housing 704 defines an interior space within which most or all of the electronic circuitry for the implantable medical device 702 is located. In the simplified example of FIG. 7, this circuitry includes an integrated circuit 708, input circuits 710-712 for each input channel, and other circuits 714 (e.g., processor circuitry, power circuitry, communication circuitry, etc.).

The integrated circuit 708 may correspond, for example, to any one of the integrated circuits 240, 326, 508, or 608 discussed above. Accordingly, the integrated circuit 708 may include a detector circuit configured to detect an MRI gradient signal and generate a corresponding control signal, a sensing circuit configured to sense cardiac signals, and, in some embodiments (e.g., corresponding to FIGS. 2 and 5), at least one MRI gradient rejection circuit configured to reject an MRI gradient signal component of a signal received via an implantable lead.

The input circuits 710-710 may correspond, for example, to any of the input circuits described above at FIGS. 2, 3, 5, and 6. Thus, in some embodiments (e.g., corresponding to FIGS. 2 and 5), each of the input circuits may comprise HV protect circuits and MRI filters. In other embodiments, (e.g., corresponding to FIGS. 3 and 6), each of the input circuits may comprise MRI filters, as well as combined HV protect and MRI gradient rejection circuits that in some aspects are configured to reject an MRI gradient signal component of a signal received via an implantable lead. In such a case, control signals 740 from the detector circuit in the integrated circuit 708 control the combined HV protect and MRI gradient rejection circuits in the input circuits.

The header 706 includes connectors 716 and 718 that are configured to receive implantable leads 720 and 722, respectively, and to couple lead conductors to device conductors that are, in turn, coupled to electronic circuitry of the implantable medical device 702. Specifically, the connector 716 couples a lead conductor 724 with a device conductor 726, while the connector 718 couples a lead conductor 728 with a device conductor 730. The device conductor 726 is routed through a feedthrough 734 in the housing 704 to the input circuit 710 (e.g., corresponding to a first input channel). The device conductor 730 is routed through a feedthrough 736 to the input circuit 712 (e.g., corresponding to a second input channel). Typically, the feedthroughs in the housing 704 are hermetically sealed.

The MRI gradient rejection circuits in the housing 704 may be coupled directly or indirectly to the lead conductors and/or the sensing circuit. For example, in embodiments corresponding to FIGS. 2 and 5, an input terminal of a MRI gradient rejection circuit is coupled to a lead conductor via an MRI RF filter and a HV protect circuit, while an output terminal of the MRI gradient active rejection circuit is directed coupled to the sensing circuit. As another example, in embodiments corresponding to FIGS. 3 and 6, an input terminal of a MRI gradient rejection circuit (that also provides HV protection) is directly coupled to a lead conductor, while an output terminal of the MRI gradient active rejection circuit is coupled to the sensing circuit via an MRI RF filter.

FIG. 7 also illustrates an embodiment where a conductor 732 that is used for detecting an MRI gradient signal is routed from the integrated circuit 708 through a feedthrough 738 of the housing 706 into the header 706. In this way, the conductor 732 may more effectively be influenced by the MRI gradient signal since at least a portion of the conductor 732 is outside of the housing 706. As discussed above, in some embodiments, the conductor may be coupled to a lead conductor (connection not shown in FIG. 7).

Exemplary Cardiac Device

The following description sets forth an exemplary implantable cardiac device (e.g., a stimulation device such as an implantable cardioverter defibrillator, a pacemaker, etc.) that is capable of being used in connection with the various embodiments that are described herein. It is to be appreciated and understood that other devices (e.g., cardiac monitoring devices, neurological monitoring devices, neurological stimulation devices, etc.) may incorporate the teachings, and that the description below is given, in its specific context, to assist the reader in understanding, with more clarity, the embodiments described herein.

Figure 8:
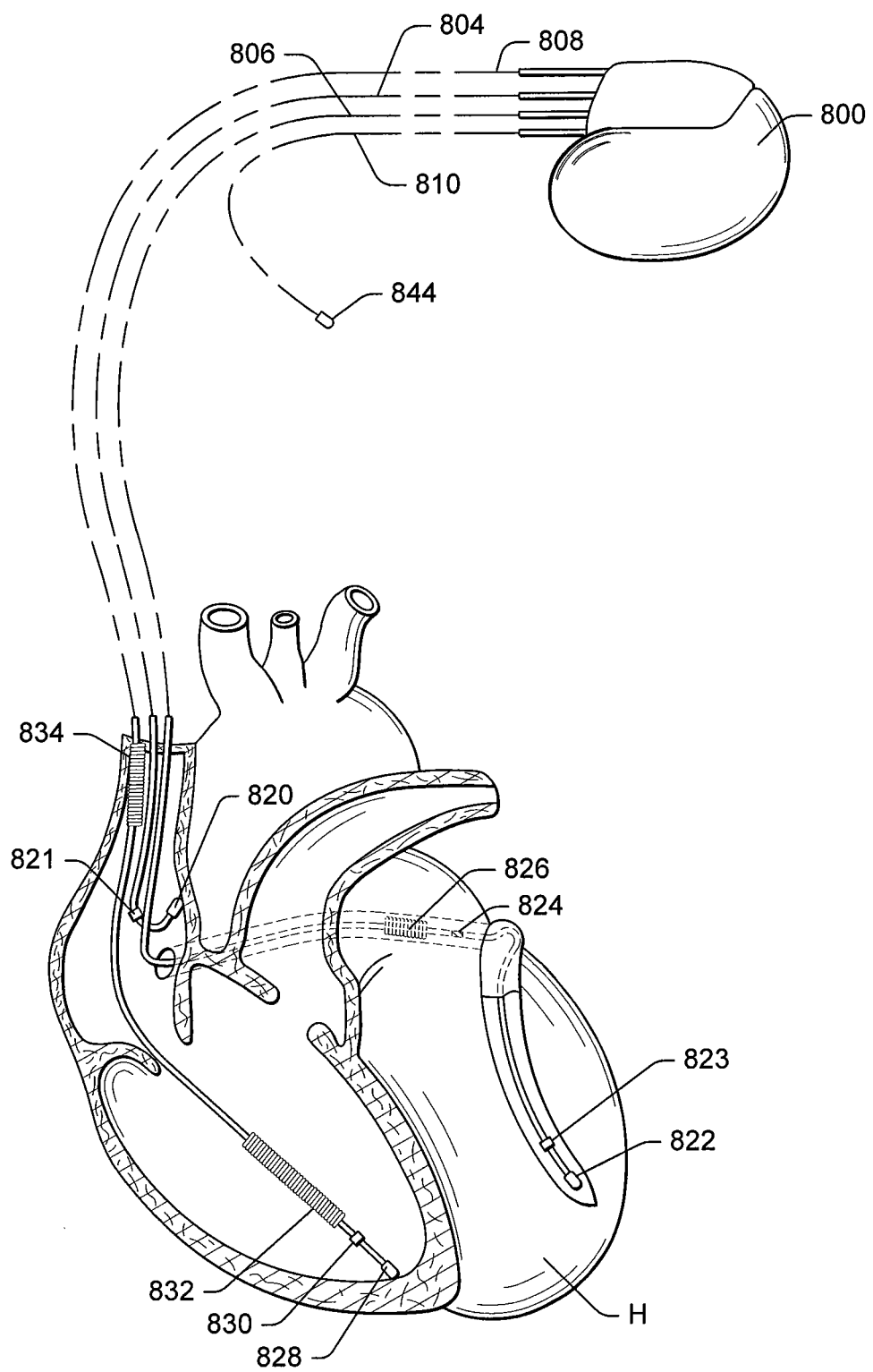
FIG. 8 is a simplified diagram of an embodiment of an implantable stimulation device in electrical communication with one or more leads implanted in a patient's heart for sensing conditions in the patient, delivering therapy to the patient, or providing some combination thereof.

FIG. 8 shows an exemplary implantable cardiac device 800 in electrical communication with a patient's heart H by way of three leads 804, 806, and 808, suitable for delivering multichamber stimulation and shock therapy. Bodies of the leads 804, 806, and 808 may be formed of silicone, polyurethane, plastic, or similar biocompatible materials to facilitate implant within a patient. Each lead includes one or more conductors, each of which may couple one or more electrodes incorporated into the lead to a connector on the proximal end of the lead. Each connector, in turn, is configured to couple with a complimentary connector (e.g., implemented within a header) of the device 800.

To sense atrial cardiac signals and to provide right atrial chamber stimulation therapy, the device 800 is coupled to an implantable right atrial lead 804 having, for example, an atrial tip electrode 820, which typically is implanted in the patient's right atrial appendage or septum. FIG. 8 also shows the right atrial lead 804 as having an optional atrial ring electrode 821.

To sense left atrial and ventricular cardiac signals and to provide left chamber pacing therapy, the device 800 is coupled to a coronary sinus lead 806 designed for placement in the coronary sinus region via the coronary sinus for positioning one or more electrodes adjacent to the left ventricle, one or more electrodes adjacent to the left atrium, or both. As used herein, the phrase "coronary sinus region" refers to the vasculature of the left ventricle, including any portion of the coronary sinus, the great cardiac vein, the left marginal vein, the left posterior ventricular vein, the middle cardiac vein, the small cardiac vein or any other cardiac vein accessible by the coronary sinus.

Accordingly, an exemplary coronary sinus lead 806 is designed to receive atrial and ventricular cardiac signals and to deliver left ventricular pacing therapy using, for example, a left ventricular tip electrode 822 and, optionally, a left ventricular ring electrode 823; provide left atrial pacing therapy using, for example, a left atrial ring electrode 824; and provide shocking therapy using, for example, a left atrial coil electrode 826 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The device 800 is also shown in electrical communication with the patient's heart H by way of an implantable right ventricular lead 808 having, in this implementation, a right ventricular tip electrode 828, a right ventricular ring electrode 830, a right ventricular (RV) coil electrode 832 (or other electrode capable of delivering a shock), and a superior vena cava (SVC) coil electrode 834 (or other electrode capable of delivering a shock). Typically, the right ventricular lead 808 is transvenously inserted into the heart H to place the right ventricular tip electrode 828 in the right ventricular apex so that the RV coil electrode 832 will be positioned in the right ventricle and the SVC coil electrode 834 will be positioned in the superior vena cava. Accordingly, the right ventricular lead 808 is capable of sensing or receiving cardiac signals, and delivering stimulation in the form of pacing and shock therapy to the right ventricle.

The device 800 is also shown in electrical communication with a lead 810 including one or more components 844 such as a physiologic sensor. The component 844 may be positioned in, near or remote from the heart.

It should be appreciated that the device 800 may connect to leads other than those specifically shown. In addition, the leads connected to the device 800 may include components other than those specifically shown. For example, a lead may include other types of electrodes, sensors or devices that serve to otherwise interact with a patient or the surroundings.

Figure 9:
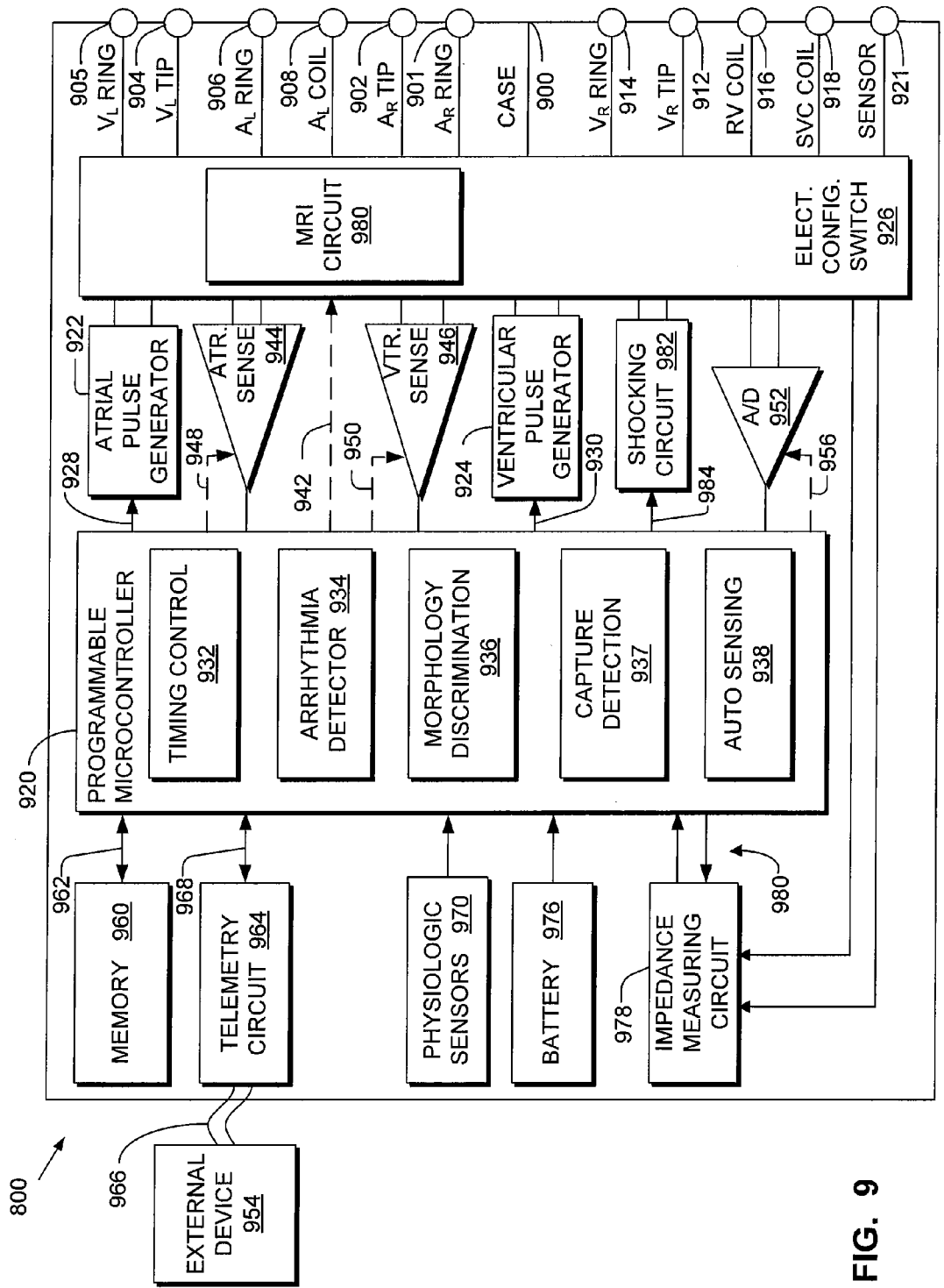
FIG. 9 is a simplified functional block diagram of an embodiment of an implantable cardiac device, illustrating basic elements that may be configured to sense conditions in the patient, deliver therapy to the patient, or provide some combination thereof.

FIG. 9 depicts an exemplary, simplified block diagram illustrating sample components of the device 800. The device 800 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

A housing 900 for the device 800 is often referred to as the "can", "case" or "case electrode", and may be programmably selected to act as the return electrode for all "unipolar" modes. The housing 900 may further be used as a return electrode alone or in combination with one or more of the coil electrodes 826, 832 and 834 for shocking purposes. The housing 900 may be constructed of a biocompatible material (e.g., titanium) to facilitate implant within a patient.

The housing 900 further includes a connector (not shown) having a plurality of terminals 901, 902, 904, 905, 906, 908, 912, 914, 916 and 918 (shown schematically and, for convenience, the names of the electrodes to which they are connected are shown next to the terminals). The connector may be configured to include various other terminals (e.g., terminal 921 coupled to a sensor or some other component) depending on the requirements of a given application.

To achieve right atrial sensing and pacing, the connector includes, for example, a right atrial tip terminal (AR TIP) 902 adapted for connection to the right atrial tip electrode 820. A right atrial ring terminal (AR RING) 901 may also be included and adapted for connection to the right atrial ring electrode 821. To achieve left chamber sensing, pacing, and shocking, the connector includes, for example, a left ventricular tip terminal (VL TIP) 904, a left ventricular ring terminal (VL RING) 905, a left atrial ring terminal (AL RING) 906, and a left atrial shocking terminal (AL COIL) 908, which are adapted for connection to the left ventricular tip electrode 822, the left ventricular ring electrode 823, the left atrial ring electrode 824, and the left atrial coil electrode 826, respectively.

To support right chamber sensing, pacing, and shocking, the connector further includes a right ventricular tip terminal (VR TIP) 912, a right ventricular ring terminal (VR RING) 914, a right ventricular shocking terminal (RV COIL) 916, and a superior vena cava shocking terminal (SVC COIL) 918, which are adapted for connection to the right ventricular tip electrode 828, the right ventricular ring electrode 830, the RV coil electrode 832, and the SVC coil electrode 834, respectively.

At the core of the device 800 is a programmable microcontroller 920 that controls the various modes of stimulation therapy. As is well known in the art, microcontroller 920 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 920 includes the ability to process or monitor input signals (data or information) as controlled by a program code stored in a designated block of memory. The type of microcontroller is not critical to the described implementations. Rather, any suitable microcontroller 920 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 9 also shows an atrial pulse generator 922 and a ventricular pulse generator 924 that generate pacing stimulation pulses for delivery by the right atrial lead 804, the coronary sinus lead 806, the right ventricular lead 808, or some combination of these leads via an electrode configuration switch 926. It is understood that in order to provide stimulation therapy in each of the four chambers of the heart, the atrial and ventricular pulse generators 922 and 924 may include dedicated, independent pulse generators, multiplexed pulse generators, or shared pulse generators. The pulse generators 922 and 924 are controlled by the microcontroller 920 via appropriate control signals 928 and 930, respectively, to trigger or inhibit the stimulation pulses.

Microcontroller 920 further includes timing control circuitry 932 to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, etc., as known in the art.

Microcontroller 920 further includes an arrhythmia detector 934. The arrhythmia detector 934 may be utilized by the device 800 for determining desirable times to administer various therapies. The arrhythmia detector 934 may be implemented, for example, in hardware as part of the microcontroller 920, or as software/firmware instructions programmed into the device 800 and executed on the microcontroller 920 during certain modes of operation.

Microcontroller 920 may include a morphology discrimination module 936, a capture detection module 937 and an auto sensing module 938. These modules are optionally used to implement various exemplary recognition algorithms or methods. The aforementioned components may be implemented, for example, in hardware as part of the microcontroller 920, or as software/firmware instructions programmed into the device 800 and executed on the microcontroller 920 during certain modes of operation.

The electrode configuration switch 926 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 926, in response to a control signal 942 from the microcontroller 920, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 944 and ventricular sensing circuits (VTR. SENSE) 946 may also be selectively coupled to the right atrial lead 804, coronary sinus lead 806, and the right ventricular lead 808, through the switch 926 for detecting the presence of cardiac activity in each of the four chambers of the heart. Accordingly, the atrial and ventricular sensing circuits 944 and 946 may include dedicated sense amplifiers, multiplexed amplifiers, or shared amplifiers. Switch 926 determines the "sensing polarity" of the cardiac signal by selectively closing the appropriate switches, as is also known in the art. In this way, the clinician may program the sensing polarity independent of the stimulation polarity. The sensing circuits (e.g., circuits 944 and 946) are optionally capable of obtaining information indicative of tissue capture.

Each sensing circuit 944 and 946 preferably employs one or more low power, precision amplifiers with programmable gain, automatic gain control, bandpass filtering, a threshold detection circuit, or some combination of these components, to selectively sense the cardiac signal of interest. The automatic gain control enables the device 800 to deal effectively with the difficult problem of sensing the low amplitude signal characteristics of atrial or ventricular fibrillation.

The outputs of the atrial and ventricular sensing circuits 944 and 946 are connected to the microcontroller 920, which, in turn, is able to trigger or inhibit the atrial and ventricular pulse generators 922 and 924, respectively, in a demand fashion in response to the absence or presence of cardiac activity in the appropriate chambers of the heart. Furthermore, as described herein, the microcontroller 920 is also capable of analyzing information output from the sensing circuits 944 and 946, a data acquisition system 952, or both. This information may be used to determine or detect whether and to what degree tissue capture has occurred and to program a pulse, or pulses, in response to such determinations. The sensing circuits 944 and 946, in turn, receive control signals over signal lines 948 and 950, respectively, from the microcontroller 920 for purposes of controlling the gain, threshold, polarization charge removal circuitry (not shown), and the timing of any blocking circuitry (not shown) coupled to the inputs of the sensing circuits 944 and 946 as is known in the art.

For arrhythmia detection, the device 800 utilizes the atrial and ventricular sensing circuits 944 and 946 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 934 of the microcontroller 920 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 952. The data acquisition system 952 is configured (e.g., via signal line 956) to acquire intracardiac electrogram ("IEGM") signals or other signals, convert the raw analog data into a digital signal, and store the digital signals for later processing, for telemetric transmission to an external device 954, or both. For example, the data acquisition system 952 may be coupled to the right atrial lead 804, the coronary sinus lead 806, the right ventricular lead 808 and other leads through the switch 926 to sample cardiac signals across any pair of desired electrodes.

The data acquisition system 952 also may be coupled to receive signals from other input devices. For example, the data acquisition system 952 may sample signals from a physiologic sensor 970 or other components shown in FIG. 9 (connections not shown).

The microcontroller 920 is further coupled to a memory 960 by a suitable data/address bus 962, wherein the programmable operating parameters used by the microcontroller 920 are stored and modified, as required, in order to customize the operation of the device 800 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 952), which data may then be used for subsequent analysis to guide the programming of the device 800.

Advantageously, the operating parameters of the implantable device 800 may be non-invasively programmed into the memory 960 through a telemetry circuit 964 in telemetric communication via communication link 966 with the external device 954, such as a programmer, transtelephonic transceiver, a diagnostic system analyzer or some other device. The microcontroller 920 activates the telemetry circuit 964 with a control signal (e.g., via bus 968). The telemetry circuit 964 advantageously allows intracardiac electrograms and status information relating to the operation of the device 800 (as contained in the microcontroller 920 or memory 960) to be sent to the external device 954 through an established communication link 966.

The device 800 can further include one or more physiologic sensors 970. In some embodiments the device 800 may include a "rate-responsive" sensor that may provide, for example, information to aid in adjustment of pacing stimulation rate according to the exercise state of the patient. One or more physiologic sensors 970 (e.g., a pressure sensor) may further be used to detect changes in cardiac output, changes in the physiological condition of the heart, or diurnal changes in activity (e.g., detecting sleep and wake states). Accordingly, the microcontroller 920 responds by adjusting the various pacing parameters (such as rate, A-V Delay, V-V Delay, etc.) at which the atrial and ventricular pulse generators 922 and 924 generate stimulation pulses.

While shown as being included within the device 800, it is to be understood that a physiologic sensor 970 may also be external to the device 800, yet still be implanted within or carried by the patient. Examples of physiologic sensors that may be implemented in conjunction with the device 800 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), which patent is hereby incorporated by reference.

The one or more physiologic sensors 970 may optionally include one or more of components to help detect movement (via, e.g., a position sensor or an accelerometer) and minute ventilation (via an MV sensor) in the patient. Signals generated by the position sensor and MV sensor may be passed to the microcontroller 920 for analysis in determining whether to adjust the pacing rate, etc. The microcontroller 920 may thus monitor the signals for indications of the patient's position and activity status, such as whether the patient is climbing up stairs or descending down stairs or whether the patient is sitting up after lying down.

The device 800 additionally includes a battery 976 that provides operating power to all of the circuits shown in FIG. 9. For a device 800 which employs shocking therapy, the battery 976 is capable of operating at low current drains (e.g., preferably less than 10 μA) for long periods of time, and is capable of providing high-current pulses (for capacitor charging) when the patient requires a shock pulse (e.g., preferably, in excess of 2 A, at voltages above 200 V, for periods of 10 seconds or more). The battery 976 also desirably has a predictable discharge characteristic so that elective replacement time can be detected. Accordingly, the device 800 preferably employs lithium or other suitable battery technology.

The device 800 can further include magnet detection circuitry (not shown), coupled to the microcontroller 920, to detect when a magnet is placed over the device 800. A magnet may be used by a clinician to perform various test functions of the device 800 and to signal the microcontroller 920 that the external device 954 is in place to receive data from or transmit data to the microcontroller 920 through the telemetry circuit 964.

The device 800 further includes an impedance measuring circuit 978 that is enabled by the microcontroller 920 via a control signal 980. The known uses for an impedance measuring circuit 978 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 800 has been implanted; measuring stroke volume; and detecting the opening of heart valves, etc. The impedance measuring circuit 978 is advantageously coupled to the switch 926 so that any desired electrode may be used.

In the case where the device 800 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 920 further controls a shocking circuit 982 by way of a control signal 984. The shocking circuit 982 generates shocking pulses of low (e.g., up to 0.5 J), moderate (e.g., 0.5 J to 10 J), or high energy (e.g., 11 J to 40 J), as controlled by the microcontroller 920. Such shocking pulses are applied to the patient's heart H through, for example, two shocking electrodes and as shown in this embodiment, selected from the left atrial coil electrode 826, the RV coil electrode 832 and the SVC coil electrode 834. As noted above, the housing 900 may act as an active electrode in combination with the RV coil electrode 832, as part of a split electrical vector using the SVC coil electrode 834 or the left atrial coil electrode 826 (i.e., using the RV electrode as a common electrode), or in some other arrangement.

Cardioversion level shocks are generally considered to be of low to moderate energy level (so as to minimize pain felt by the patient), be synchronized with an R-wave, pertain to the treatment of tachycardia, or some combination of the above. Defibrillation shocks are generally of moderate to high energy level (i.e., corresponding to thresholds in the range of 5 J to 40 J), delivered asynchronously (since R-waves may be too disorganized), and pertaining to the treatment of fibrillation. Accordingly, the microcontroller 920 is capable of controlling the synchronous or asynchronous delivery of the shocking pulses.

As mentioned above, the device 800 may include several components that provide MRI rejection-related functionality as taught herein. For example, as shown in FIG. 9, the switch 926 may include or be implemented in conjunction with an MRI circuit 980 that provides MRI gradient signal detection, MRI gradient signal rejection, and MRI RF signal filtering as discussed above.

It should be appreciated that various modifications may be incorporated into the disclosed embodiments based on the teachings herein. For example, the structure and functionality taught herein may be incorporated into types of devices other than the specific types of devices described above. In addition, different types of active components (e.g., different types of transistors or amplifier circuits) may be used to sense MRI gradient signals and/or reject MRI gradient signals.

The various structures and functions described herein may be incorporated into a variety of apparatuses (e.g., a stimulation device, a monitoring device, a cardiac device, a neurological device, etc.) and implemented in a variety of ways.

Different embodiments of such an apparatus may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements. In addition, terminology of the form "at least one of A, B, or C" or "one or more of A, B, or C" or "at least one of the group consisting of A, B, and C" used in the description or the claims means "A or B or C or any combination of these elements."

As used herein, the term "determining" encompasses a wide variety of actions. For example, "determining" may include calculating, computing, processing, deriving, investigating, looking up (e.g., looking up in a table, a database or another data structure), ascertaining, and the like. Also, "determining" may include receiving (e.g., receiving information), accessing (e.g., accessing data in a memory), and the like. Also, "determining" may include resolving, selecting, choosing, establishing, and the like.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above it will be understood that the teachings herein are intended to cover any changes, adaptations or modifications which are within the scope of the disclosure.

What is claimed is:

1. An apparatus for rejecting MRI gradient signals in an implantable medical device, comprising:
   a detector circuit configured to detect an MRI gradient signal and generate a control signal based on the detected MRI gradient signal; and
   an MRI gradient active rejection circuit coupled to the detector circuit, the MRI gradient active rejection circuit comprising a transistor biased to operate within a linear region by the control signal when the detector circuit detects an MRI gradient signal to reject an MRI gradient signal component of a signal received via an implantable lead to provide an output signal, wherein the rejection of the MRI gradient signal is based on the control signal.

2. The apparatus of claim 1, wherein the detector circuit comprises an amplifier circuit.

3. The apparatus of claim 1, wherein the detector circuit comprises a filter circuit having a bandwidth of less than 5 MHz.

4. The apparatus of claim 1, wherein an input of the detector circuit is coupled to a conductor configured to acquire the MRI gradient signal if the implantable medical device is subjected to an MRI field.

5. The apparatus of claim 4, wherein the conductor is routed through a hermetically sealed feedthrough of a housing of the implantable medical device such that at least a portion of the conductor is outside of the housing.

6. The apparatus of claim 1, wherein the MRI gradient active rejection circuit comprises an amplifier circuit.

7. The apparatus of claim 1, wherein:
   the implantable medical device comprises a connector configured to receive the implantable lead;
   an input terminal of the MRI gradient active rejection circuit is coupled to the connector; and
   an output terminal of the MRI gradient active rejection circuit is coupled to an MRI RF filter circuit of the implantable medical device.

8. The apparatus of claim 1, wherein:
   an input terminal of the MRI gradient active rejection circuit is coupled to an MRI RF filter circuit of the implantable medical device; and
   an output terminal of the MRI gradient active rejection circuit is coupled to a signal sensing circuit of the implantable medical device.

9. The apparatus of claim 1, wherein the control signal is approximately 180 degrees out-of-phase with the detected MRI gradient signal.

10. The apparatus of claim 9, wherein the MRI gradient active rejection circuit adds the control signal to the signal received via an implantable lead to reject the MRI gradient signal component.

11. The apparatus of claim 1, wherein:
   the detector circuit comprises an amplifier circuit and has a bandwidth of less than 5 MHz;
   the control signal is approximately 180 degrees out-of-phase with the detected MRI gradient signal; and
   the MRI gradient active rejection circuit is further configured to add the control signal to the signal received via an implantable lead to reject the MRI gradient signal component.

12. The apparatus of claim 11, wherein the MRI gradient active rejection circuit comprises a transistor biased by the control signal to operate within a linear region.

13. An implantable medical device, comprising:
   a biocompatible housing comprising a feedthrough;
   a sensing circuit located within an interior space defined by the housing and configured to sense cardiac signals;
   a connector configured to couple a first conductor to an implantable lead, wherein the first conductor is routed from the connector through the feedthrough to the interior space;
   a detector circuit configured to detect an MRI gradient signal induced on a second conductor and further configured to generate a control signal based on the detected MRI gradient signal; and
   an MRI gradient active rejection circuit coupled to the first conductor and configured to reject an MRI gradient signal component of a signal received via the implantable lead to provide an output signal that is coupled to the sensing circuit, wherein the rejection of the MRI gradient signal component is based on the control signal, wherein the MRI gradient active rejection circuit comprises a transistor biased to operate within a linear region by the control signal if the implantable medical device is subjected to an MRI field.

14. The implantable medical device of claim 13, wherein:
the implantable medical device further comprises an MRI RF filter circuit;
an input terminal of the MRI gradient active rejection circuit is coupled to the first conductor;
an output terminal of the MRI gradient active rejection circuit is coupled to an input terminal of the MRI RF filter circuit; and
an output terminal of the MRI RF filter circuit is coupled to an input terminal of the sensing circuit.

15. The implantable medical device of claim 13, wherein:
the implantable medical device further comprises an MRI RF filter circuit;
an input terminal of the MRI RF filter circuit is coupled to the first conductor;
an output terminal of the MRI RF filter circuit is coupled to an input terminal of the MRI gradient active rejection circuit; and
an output terminal of the MRI gradient active rejection circuit is coupled to an input terminal of the sensing circuit.

16. The implantable medical device of claim 13, further comprising a high voltage protection circuit configured to generate another control signal to control the MRI gradient active rejection circuit to reject incoming signals, wherein the MRI gradient active rejection circuit comprises a transistor that is biased:
to turn off if the other control signal generated by the high voltage protection circuit is set to a value for rejecting high voltage signals; and
to operate within a linear region based on the control signal from the detector circuit if the other control signal generated by the high voltage protection circuit is not set to a value for rejecting high voltage signals.

17. A method for rejecting MRI gradient signals in an implantable medical device, comprising:
detecting an MRI gradient signal;
generating a control signal based on the detected MRI gradient signal; and
actively rejecting an MRI gradient signal component of a signal received via an implantable lead to provide an output signal, wherein the rejection of the MRI gradient signal component is based on the control signal, wherein the control signal is approximately 180 degrees out-of-phase with the detected MRI gradient signal and the active rejection comprises controlling a transistor via the control signal to reject the MRI gradient signal component.

* * * * *